United States Patent
Sumida et al.

(10) Patent No.: US 7,279,339 B2
(45) Date of Patent: Oct. 9, 2007

(54) REAGENT FOR AN IMMUNOASSAY

(75) Inventors: Kyoichi Sumida, Amagasaki (JP);
Minoru Fujita, Amagasaki (JP);
Hiromichi Adachi, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/867,912

(22) Filed: Jun. 15, 2004

(65) Prior Publication Data
US 2005/0069967 A1 Mar. 31, 2005

(30) Foreign Application Priority Data
Sep. 30, 2003 (JP) ............... 2003-340028

(51) Int. Cl.
*G01N 33/543* (2006.01)
(52) U.S. Cl. .............. 436/523; 436/518; 436/524; 436/528; 422/68.1; 422/82.05; 422/82.08
(58) Field of Classification Search .......... 436/501, 436/518, 523, 524, 528; 422/50, 61, 68.1, 422/82.05, 82.08, 4, 7.1; 435/7.92, 283.1, 435/287.1, 287.2, 288.7
See application file for complete search history.

(56) References Cited

U.S. PATENT DOCUMENTS

| | | | | |
|---|---|---|---|---|
| 4,210,723 A | * | 7/1980 | Dorman et al. | 435/180 |
| 4,401,765 A | * | 8/1983 | Craig et al. | 436/533 |
| 5,486,479 A | * | 1/1996 | Ito et al. | 436/533 |
| 5,879,881 A | * | 3/1999 | Rubenstein | 435/5 |
| 6,248,597 B1 | * | 6/2001 | Eda et al. | 436/518 |

FOREIGN PATENT DOCUMENTS

| | | | |
|---|---|---|---|
| EP | 0 263 731 | | 4/1988 |
| EP | 0 789 032 | | 8/1997 |
| EP | 1314982 | * | 5/2003 |
| JP | 10-123137 | | 5/1998 |
| WO | 02/18953 | * | 3/2003 |

OTHER PUBLICATIONS

Sakaki et al., Stabilization of an antibody conjugated with enzyme by 2-methacryloyloxyethyl phosphorylcholine copolymer in enzyme-linked immunosorbent assay, Journal of Biomedical Materials Research, 1999, vol. 47, No. 4, pp. 523-528.*

Gangopadhyay et al., Modification of Antibody Isoelectric Point Affects Biodistribution of 111-Indium-Labeled Antibody, Nuclear Medicine and Biology, 1996, vol. 23, pp. 257-261.*

* cited by examiner

*Primary Examiner*—Long V. Le
*Assistant Examiner*—Melanie J. Yu
(74) *Attorney, Agent, or Firm*—Hamre, Schuman, Mueller & Larson, P.C.

(57) ABSTRACT

The present invention relates to (1) A reagent for an immunoassay of a target substance existing in a free form and a bound form in a specimen, comprising a latex 1 which is immobilized with a monoclonal antibody 1 for the target substance, and a latex 2 which has a different mean particle size from the latex 1 and is immobilized with a monoclonal antibody 2 having a different recognition site for the target substance from the antibody 1, (2) An immunoassay method comprising reacting the target substance with the reagent of (1) and determining an amount of the substance based on the result of an agglutination reaction among the target substance, the latex1 and the latex2, and (3) A reagent kit comprising a reagent of (1) and a reagent containing an agglutination accelerator for an antigen-antibody reaction.

6 Claims, 1 Drawing Sheet

REAGENT FOR AN IMMUNOASSAY

BACKGROUND OF THE INVENTION

1. Technical Field

The present invention relates to a reagent for a high sensitive immunoassay method, an immunoassay method using said reagent and a reagent kit comprising said reagent.

2. Related Art

It has been known that some biological substances exist both in a free form and a bound form. A representative example thereof is the prostate-specific antigen (PSA) which has been known to exist in a bound form of PSA and $\alpha_1$-antichymotrypsin (ACT) in blood, as well as in a free form of PSA itself. Since such substances exhibit a change in a ratio of the free form and the bound form depending on an amount of substance bound with the free form as well as in vivo circumstances, both forms should be assayed in the assay of such substances. However, there is a problem that in an immunoassay of such substances by applying antigen-antibody reaction, a high precise assay is difficult due to different binding rate of the antibody to the free form and the bound form. In order to solve such the problem, JP-A-09-234068 proposes an assay reagent for equimolar reaction with both free form and bound form, and an assay method using the same are proposed. Since this method is, however, the assay method by ELISA, it can be possible to assay only in the specific equipment and is impossible to apply in the common autoanalyzer. Although the latex turbidimetry is known as a high sensitive immunoassay method by applying the common autoanalyzer, there is also a problem that the equimolar assay of both free form and bound form is difficult in such a method, even if the latex sensitized (immobilized) with the antibody which exhibits equimolar reaction in ELISA is used. Owing to these problems, a development of a method is demanded, which can assay the substance existing in the free form and the bound form in the organism and can be applied in the common autoanalyzer.

In JP-A-10-123137, an immunoassay method is disclosed, in which at least two types of different monoclonal antibodies for a specific antigen are carried by an insoluble carrier such as latex and the insoluble carrier having different mean particle diameter is used. However, in this method, the free form and the bound form in the specimen are not assayed.

DISCLOSURE OF THE INVENTION

Problems to be Solved by the Invention

An object of the present invention is to provide a reagent for immunoassay using two or more types of antibodies which are immobilized in two or more types of latex having different mean particle sizes and for equimolar assay of a substance existing both in the free form and the bound form in the organism with high sensitivity and high precision, an assay method using said reagent, and a reagent kit containing said reagent. The present invention provides the following means for solving the problems.

Means for Solving the Problems (1) A reagent for an immunoassay of a target substance existing in a free form and a bound form in a specimen, comprising a latex 1 which is immobilized with a monoclonal antibody 1 for the target substance, and a latex 2 which has a different mean particle size from the latex 1 and is immobilized with a monoclonal antibody 2 having a different recognition site for the target substance from the antibody 1.

(2) An immunoassay method for a target substance existing in a free form and a bound form in a specimen, comprising reacting the target substance with a latex 1 which is immobilized with a monoclonal antibody 1 for the target substance, and a latex 2 which has a different mean particle size from the latex 1 and is immobilized with a monoclonal antibody 2 having a different recognition site for the target substance from the antibody 1, and determining an amount of the substance based on the result of an agglutination reaction among the target substance, the latex1 and the latex2.

(3) A reagent kit for an immunoassay of a target substance existing in a free form and a bound form in a specimen, comprising a reagent for an immunoassay containing a latex 1 which is immobilized with a monoclonal antibody 1 for the target substance, and a latex 2 which has a different mean particle size from the latex 1 and is immobilized with a monoclonal antibody 2 having a different recognition site for the target substance from the antibody 1, and a reagent containing an agglutination accelerator for an antigen-antibody reaction.

Effect of the Invention

The present invention relates to the highly sensitive and highly precise reagent for immunoassay of the target substance existing in the free form and the bound form in the specimen, the assay method using said reagent, and the reagent kit containing said reagent. By using the assay method of the present invention, both target substances in the free form and the bound form can be precisely assayed in an equimolar.

DESCRIPTION OF CODES

Figure 1:
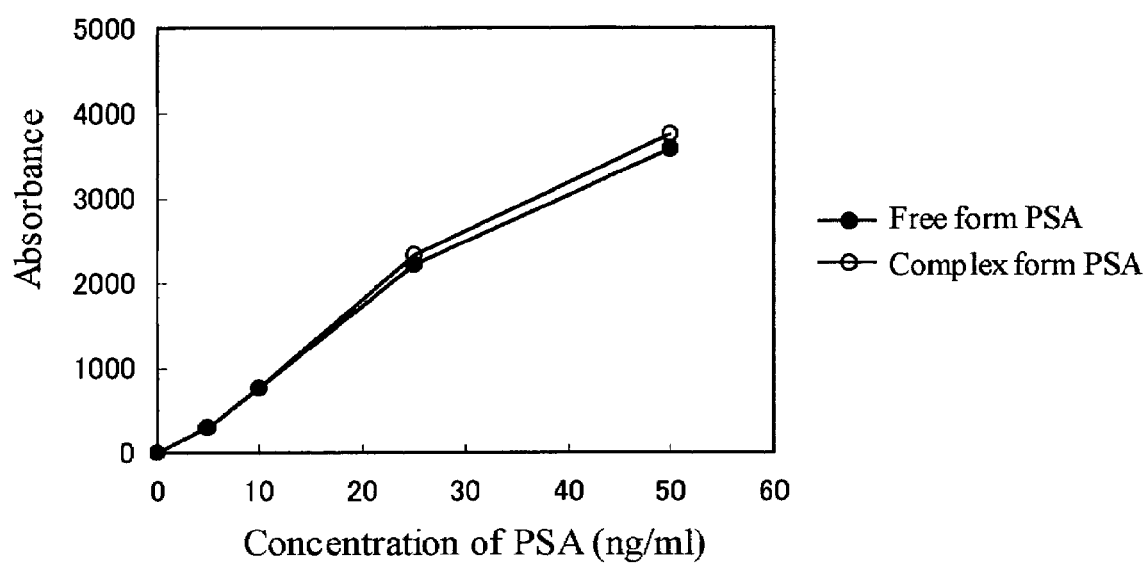
FIG. 1 shows the calibration curve prepared from the optical density of the free PSA and the complex PSA obtained in Example 2 and each concentration thereof, i.e. a comparison with the reactivity between the forms of PSA and the latex immobilizing the antibody.

A mark-●-shows assay result of Example 2 using the free form PSA, and a mark-○- shows assay result of Example 2 using the complex form PSA.

BEST MODE FOR CARRYING OUT THE INVENTION

A target substance in the present invention is not particularly limited, so long as it has the free form and the bound form, but the substance having both forms in the specimen to be assayed are preferable. The free form designated herein means, for example, the substance existing alone in the specimen such as the biological specimen. The bound form designated herein means, for example, a complex which is bound with the free form hereinabove and the substance having an affinity to the target substance (the affinity substance). Specifically, the substance having both forms includes prostate-specific antigen (PSA), protein C, elastase, cathepsin G, thrombin, $C_1$-esterase, plasmin and tissue-type plasminogen activator, and among them, a preferable example thereof is PSA. The affinity substance in the bound form is not particularly limited, so long as it is one having an affinity to the target substance and an ability to bind therewith. Specifically, $\alpha_1$-antichymotrypsin or protein C inhibitor for the case when the target substance is PSA; protein C inhibitor for the case when the target substance is protein C; $\alpha_1$-protease inhibitor for the case when the target substance is elastase; $\alpha_1$-antichymotrypsin for the case when the target substance is cathepsin G; anti-thrombin III for the case when the target substance is thrombin; $C_1$ inhibitor for the case when the target substance is $C_1$-esterase; $\alpha_2$-antiplasmin for the case when the target substance is plasmin; and plasminogen activator inhibitor 1 can be included for the case when the target substance is tissue-type plasminogen activator, respectively.

A monoclonal antibody for the target substance in the present invention is not particularly limited so long as it has reactivity with the target substance. The origin thereof is not particularly limited. Further, the monoclonal antibody of the commercially available product or the monoclonal antibody produced by the known method using cell fusion technique or gene recombination technology [Eur. J. Immunol. 6, 511 (1976)] and having properties described in the above can be used.

In the monoclonal antibody for the target substance in the present invention, Fab fragment obtained by partial degradation using papain; F(ab')$_2$ fragment obtained by partial degradation using pepsin; and Fab' fragment obtained by reduction of F(ab')$_2$ fragment, namely, antibody fragment can all be included. Such fragments are preferably used, because the non-specific reaction can be avoided in the assay of the target substance.

Two or more types of the monoclonal antibody for the target substance in the present invention have the different antibody recognition site in the target substance. In the case when two types of the monoclonal antibody are used, the one having the acidic isoelectric point (pI) and the other having the neutral isoelectric point are preferably used. Specific examples of the acidic pI are 3-5, preferably 4-5, and the neutral pI are 6-8, preferably 7-8. Further, in the case when three or more types of the antibody are used, the antibody having pI according to the above may be used.

A latex used in the present invention is not particularly limited so long as it is commonly used in this field. Preferable examples thereof are styrene-based latex such as polystyrene latex, and acrylic acid-based latex. Among these latex particles, the polystyrene latex particles obtained by emulsion polymerization without using emulsifying agent are most preferable, because they can adsorb protein or peptide smoothly due to strong hydrophobic surface thereof and have properties to be stably dispersed in a solution without using any emulsifying agent due to repulsive force of negative charges on the surface. Various modified latex (e.g. carboxylic acid modified latex, in which carboxyl group is introduced into the above polystyrene) and magnetic latex (a latex including magnetic particles) can also be used if necessary.

The latex used in the present invention may be commercially available latex, and the latex particle having small mean particle size, namely, one having large surface area per unit weight is preferable due to sensitizing the antibody on the surface effectively. Specifically, two types of particles having different mean particle sizes selected from particles generally having 0.05-2.4 μm, preferably 0.05-1.0 μm, more preferably 0.05-0.28 μm, can preferably be used in combination. In a preferable combination of particle sizes, one is selected from the range of particle size of generally 0.05-0.3, preferably 0.05-0.18 μm, and the other is selected from the range of particle size of generally 0.18-0.5, preferably 0.18-0.28 μm. Equimolar assay of the target substance existing both in the free form and the bound form can be performed by using the latex particles having such different mean particle sizes in combination. In addition, difference between the particle sizes of two types of the latex should preferably be at least 0.05 nm.

A reagent for an immunoassay of the present invention comprises a latex which is immobilized with a monoclonal antibody for the target substance, and another latex which has a different mean particle size from the above latex and is immobilized with a monoclonal antibody having a different recognition site from the antibody in the target substance. Specifically, for example, in the case when the target substance is PSA, the reagent comprising the latex immobilized with PSA monoclonal antibody having, for example, a mean particle size of 0.05-0.18 μm, and the latex immobilized with PSA antibody having the recognition site different from the above PSA antibody having, for example, a mean particle size of 0.18-0.28 μm can be included. Using the latexes having such particle sizes, equimolar assay of the free form and the bound form can be performed. When two types of latexes are mixed, a ratio of volumes is preferably 1:10-10:1, more preferably 1:10-2:1, in the ratio of latexes having larger and smaller mean particle sizes. In the case of using three or more types, two types thereof are set to be the above ratio, and other type is set to a volume depending on the above.

A solvent used for preparing the reagent may be any solvent so long as it does not have a property to inhibit binding the monoclonal antibody with the target substance, and include, for example, buffer solution having buffering action around the neutral range at pH 5.0-10.0, preferably at pH 6.5-8.5, such as phosphate buffer, Tris buffer, Good's buffer, glycine buffer and borate buffer. Concentration of buffering agent in the buffer is generally selected from a range of 10-500 mM, preferably 10-300 mM. Further, the solution may contain, for example, sugars, salts such as NaCl, surface active agents and antiseptics, so long as the amount thereof does not inhibit binding the monoclonal antibody with the target substance.

A method for immobilizing the monoclonal antibody with the latex can be performed according to the known method. For example, the monoclonal antibody and the latex are suspended in the buffer, reacted at 20-30° C. for 2-3 hours, and the mixture is treated with centrifugation, blocking, and the like, which are commonly performed as post-treatment in this field, to obtain the immobilized monoclonal antibody with latex.

A reagent kit for immunoassay of the present invention is not particularly limited, so long as the kit comprises the above described reagent for the immunoassay of the present invention and the reagent containing agglutination accelerator for antigen-antibody reaction. The agglutination accelerator for the antigen-antibody reaction may be any substance having accelerating action for the agglutination reaction of the antigen-antibody reaction. Specifically, the accelerator includes, for example, a polymer having a side chain of the group represented by the following general formula [1]:

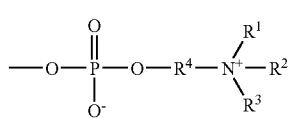

[1]

(wherein each of R¹-R³ is an alkyl group optionally having a hydrogen atom or a hydroxyl group independently, and R⁴ is an alkylene group). More specifically, the accelerator includes a polymer having a monomer unit derived from the monomer represented by the following general formula [2]:

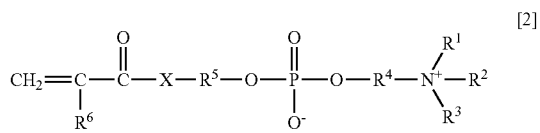

[2]

(wherein R⁵ is an alkylene group optionally having a substituent and an oxygen atom in the chain, R⁶ is a hydrogen atom or a methyl group, X is an oxygen atom or a —NH— group, and R¹-R⁴ are the same as the above)

In the above general formula [1] or [2], the alkyl group of R¹-R³ optionally having a hydroxyl group maybe any of straight, branched and cyclic chains, and is a group generally having 1-6 carbon atoms, preferably 1-4 carbon atoms, more preferably 1-2 carbon atoms, and most preferably 1 carbon atom. Specifically, the alkyl group includes, for example, methyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, tert-hexyl, cyclopropyl, cyclohexyl and cyclopentyl groups. Among them, methyl and ethyl groups are preferable, and methyl group is more preferable.

The alkyl group having a hydroxyl group includes an alkyl group, in which 1-2 hydrogen atoms, preferably 1 hydrogen atom, is substituted by a hydroxyl group. Specifically, the alkyl group having a hydroxyl group includes, for example, hydroxymethyl, hydroxyethyl, hydroxy-n-propyl, hydroxy-isopropyl, hydroxy-n-butyl, hydroxy-isobutyl, hydroxy-sec-butyl, hydroxy-tert-butyl, hydroxy-n-pentyl, hydroxy-isopentyl, hydroxy-sec-pentyl, hydroxy-tert-pentyl, hydroxy-n-hexyl, hydroxy-isohexyl, hydroxy-sec-hexyl, hydroxy-tert-hexyl, hydroxy-cyclopropyl, hydroxy-cyclohexyl and hydroxy- cyclopentyl groups. Among them, hydroxymethyl and hydroxyethyl groups are preferable.

The alkylene group represented by R⁴ includes, for example, an alkylene group having 1-6 carbon atoms, preferably 2-3 carbon atoms, and may be any of straight, branched and cyclic chains. Specifically, the alkylene group includes, for example, methylene, ethylene, propylene, trimethylene, butylene, 1-ethylehtylene, 2-methyltrimethylene, 2-ethyltrimethylene, hexylene, cyclopropylene, cyclobutylene, cyclopentylene and cyclohexylene groups. Among them, preferable examples are ethylene, propylene and trimethylene groups.

In the alkylene group represented by R⁵ optionally having a substituent and an oxygen atom in the chain in the general formula [2], examples of the alkylene group without an oxygen atom include, for example, the alkylene group having 1-10 carbon atoms, preferably 1-6 carbon atoms, more preferably 2-6 carbon atoms, which may be any of straight, branched and cyclic chains. Specifically, the alkylene group includes, for example, methylene, ethylene, propylene, trimethylene, butylene, 1-ethylehtylene, 2-methyltrimethylene, 2-ethyltrimethylene, hexylene, cyclopropylene, cyclobutylene, cyclopentylene and cyclohexylene groups. Examples of the substituent include an alkoxyl group having 1-6 carbon atoms, preferably 1-3 carbon atoms (which may be any of straight, branched and cyclic chains). More specifically, the substituent includes, for example, methoxy, ethoxy, n-propoxy, isopropoxy, n-butoxy, isobutoxy, sec-butoxy, tert-butoxy, n-pentyloxy, isopentyloxy, sec-pentyloxy, tert-pentyloxy, n-hexyloxy, isohexyloxy, sec-hexyloxy, tert-hexyloxy, cyclopropoxy, cyclohexyloxy and cyclopentyloxy groups. Further, the substituent includes a halogen atom such as fluorine atom, chlorine atom, bromine atom and iodine atom. Among them, preferable examples are ethylene, propylene, trimethylene and butylene groups. In the case of the substituent having oxygen atoms in the chain, the number of oxygen atom are 1-5, preferably 1-3, and more specifically, the substituent includes a group of —(C₂H₄O)ₙ—C₂H₄—, wherein n is an integer of 1-5. In the alkylene group represented by R⁵ optionally having a substituent and an oxygen atom in the chain hereinabove, ethylene and propylene groups are preferable, and ethylene group is more preferable.

A polymer having a constitutional unit based on the monomer having the group represented by the general formula [1] hereinabove as a side chain, may be a commercially available product, or a product synthesized by the methods described in JP-A-10-45794, JP-A-2000-239696 or the like.

A constitutional unit based on the monomer represented by the general formula [2] hereinabove includes a constitutional unit having the above described R¹-R⁶, and specifically includes a constitutional unit based on the monomer represented by the following general formula [5]:

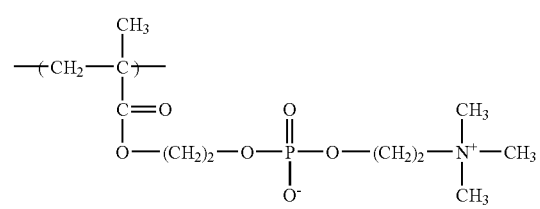

[5]

In the case when the polymer having the constitutional unit based on the monomer represented by the general formula [2] hereinabove is a copolymer, examples of the monomer unit other than the constitutional unit based on the monomer represented by the general formula [2] hereinabove can be the monomer unit derived from the monomer selected from a group consisting of acrylic acid or acrylates thereof, methacrylic acid or methacrylates thereof, acrylamide or N-substited acrylamides, methacrylamide or N-substited methacrylamides, and styrene or derivatives thereof. Two or more types of these monomer units may be contained in the copolymer. A ratio of the constitutional unit based on the monomer represented by the general formula [2] hereinabove is generally 20% and more to under 100%, preferably 30 to 95%, more preferably 30 to 90%.

In the monomer unit other than the constitutional unit based on the monomer represented by the general formula [2] hereinabove, the acrylate includes alkyl acrylate and aralkyl acrylate; and the methacrylate includes alkyl methacrylate and aralkyl methacrylate. The N-substited acrylamide includes N-alkyl acrylamide and N-aralkyl acrylamide. The N-substited methacrylamide includes N-alkyl methacrylamide and N-aralkyl methacrylamide. The styrene derivatives include α-methyl styrene and styrene or α-methyl styrene having a substituent.

An alkyl group in the above described alkyl acrylate, alkyl methacrylate, N-alkyl acrylamide and N-alkyl methacrylamide may be any of straight, branched and cyclic chains, and carbon atoms thereof are generally 1-6, and more preferably 1-4. Specifically, the alkyl group includes, for example, methyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, tert-hexyl, cyclopropyl, cyclohexyl and cyclopentyl groups. The alkyl group may optionally have a substituent, which includes hydroxyl group, lower-alkoxyl group having 1-3 carbon atoms and trialkylammonio group (An alkyl group thereof includes, for example, an alkyl group having 1-3 carbon atoms such as methyl, ethyl, propyl and isopropyl groups. When the substituent is trialkylammonio group, since the substituent is positively charged, a counter anion is generally bound. Such counter anion includes a halide ion such as fluoride ion, chloride ion, bromide ion and iodide ion). The alkyl group having a substituent includes, for example, a group represented by the following formula:

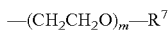
—(CH$_2$CH$_2$O)$_m$—R$^7$ (wherein R$^7$ is an alkyl group having 1-3 carbon atoms and m is 1-100).

An aralkyl group in the above described aralkyl acrylate, aralkyl methacrylate, N-aralkyl acrylamide and N-aralkyl methacrylamide includes the one having 1-10 carbon atoms. Specifically, the aralkyl group includes, for example, benzyl, phenylethyl, phenylpropyl and phenylbutyl groups.

A substituent for styrene or α-methyl styrene includes, for example, an alkyl group which generally has straight, branched or cyclic chain having 1-6 carbon atoms, preferably 1-4 carbon atoms (specifically, for example, methyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, tert-hexyl, cyclopropyl, cyclohexyl and cyclopentyl groups); for example, an aralkyl group which generally has straight, branched or cyclic chain having 1-6 carbon atoms, preferably 1-4 carbon atoms (specifically, for example, methoxy, ethoxy, n-propoxy, isopropoxy, n-butoxy, isobutoxy, sec-butoxy, tert-butoxy, n-pentyloxy, isopentyloxy, sec-pentyloxy, tert-pentyloxy, n-hexyloxy, isohexyloxy, sec-hexyloxy, tert-hexyloxy, cyclopropoxy, cyclohexyloxy and cyclopentyloxy groups); a halogen atom such as fluorine atom, chlorine atom, bromine atom and iodine atom, carboxyl group, hydroxy group and amino group.

A monomer unit other than the constitutional unit based on the monomer represented by the general formula [2] hereinabove includes, for example, a monomer unit derived from methacrylic acid, methyl methacrylate, ethyl methacrylate, propyl methacrylate, butyl methacrylate, dodecyl methacrylate, octadecyl methacrylate, 2-ethylhexyl methacrylate, lauryl methacrylate, stearyl methacrylate, 2-trimethylammonioethyl methacrylate, benzyl methacrylate, phenylethyl methacrylate, acrylic acid, methyl acrylate, ethyl acrylate, butyl acrylate, 2-ethylhexyl acrylate, lauryl acrylate, stearyl acrylate, 2-trimethylammonioethyl acrylate, benzyl acrylate, phenylethyl acrylate, acrylamide, N-methyl acrylamide, N-ethyl acrylamide, N-butyl acrylamide, N-2-ethylhexyl acrylamide, N-lauryl acrylamide, N-stearyl acrylamide, N-2-trimethylammonioethyl acrylamide, N-benzyl acrylamide, N-phenylethyl acrylamide, methacrylamide, N-methyl methacrylamide, N-ethyl methacrylamide, N-butyl methacrylamide, N-2-ethylhexyl methacrylamide, N-lauryl methacrylamide, N-stearyl methacrylamide, N-2-trimethylammonioethyl methacrylamide, N-benzyl methacrylamide, N-phenylethyl methacrylamide, styrene, carboxystyrene, hydroxystyrene, aminostyrene, methylstyrene, ethylstyrene, methoxystyrene, ethoxystyrene, chlorostyrene, bromostyrene, α-methylstyrene, α-methyl-carboxystyrene, α-methyl-hydroxystyrene, α-methyl-aminostyrene, α-methyl-methylstyrene, α-methyl-ethylstyrene, α-methyl-methoxystyrene, α-methyl-ethoxystyrene, α-methyl-chlorostyrene, α-methyl-bromostyrene, N,N,N-triethylammoniumethyl methacrylate bromide, N,N,N-trimethylammoniumethyl methacrylate chloride, N,N-diethyl-N-propylammoniumethyl methacrylate bromide, N,N,N-trimethylammonium-2-hydroxypropyl methacrylate chloride (QM), and N,N,N-trimethylammoniummethyl styrene bromide. Further, a monomer unit represented by the following general formula [4] can also be exemplified:

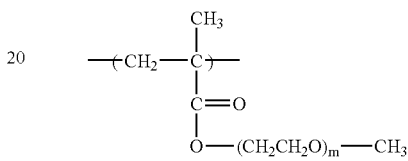

(wherein m is 1-100).

Among the above exemplified monomer units, the monomer unit derived from methacrylic acid, stearyl methacrylate, benzyl methacrylate, butyl methacrylate, dodecyl methacrylate, octadecyl methacrylate and N,N,N-trimethylammonium-2-hydroxypropyl methacrylate chloride (QM), and the monomer unit represented by the general formula [4] are preferable.

In the agglutination accelerator hereinabove, a polymer comprising the monomer unit represented by the following general formula [5];

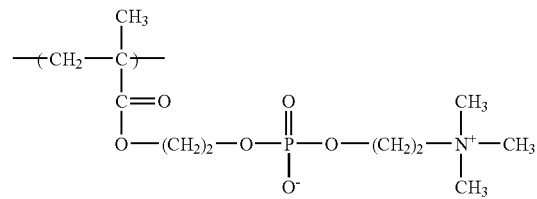

a copolymer comprising the monomer unit represented by the general formula [5] and butyl methacrylate; a copolymer comprising the monomer unit represented by the general formula [5] and the monomer unit represented by the general formula [4] hereinabove; a copolymer comprising the monomer unit represented by the general formula [5] and octadecyl methacrylate; a copolymer comprising the monomer unit represented by the general formula [5] and octadodecyl methacrylate; and a copolymer comprising the monomer unit represented by the general formula [5] and benzyl methacrylate are preferable. Among them, the copolymer comprising the monomer unit represented by the general formula [5] and benzyl methacrylate is more preferable.

Concentration of the agglutination accelerator hereinabove in the reaction is generally 0.1-20 w/v %, preferably 0.1-10 w/v %, more preferably 0.1-5 w/v %. Two or more types of the above agglutination accelerator may be used, and in such a case, a concentration range is preferably set as described above.

Production process of the monomer and the polymer used as the agglutination accelerator hereinabove can be performed according to the description in JP-A-2002-365296.

Guanidine, guanidine salts or derivatives thereof as a nonspecific reaction suppressor may be added to the reagent containing agglutination accelerator for antigen-antibody reaction. The guanidine salts include, for example, guanidine hydrochloride, guanidine carbonate, guanidine thiocyanate, guanidine sulfate, guanidine nitrate and guanidine phosphate. The guanidine derivatives include, for example, arginine, guanidinobenzoic acid, guanidinoacetic acid, guanidinosuccinic acid and guanidinoacetic acid. Two or more additives may be added. Amount of the additive is not particularly limited, so long as the objective effect can be obtained. Preferable amount of the additive is generally set to the concentration of 10-700 mM in the reagent, and 7.5-525 mM during the reaction.

The solvent used for preparation of the reagent containing agglutination accelerator for antigen-antibody reaction in the present invention is same as used in the reagent for assay of the present invention.

Immunoassay method of the present invention comprises reacting a specimen (for example, serum, plasma, urine, spinal fluid, extract solution of human tissue or human cells, etc.) containing the target substance existing in the free form and the bound form in the organism or in the specimen, with a reagent containing the latex 1 immobilized with the monoclonal antibody 1 for the target substance and the latex 2 having a mean particle size different from the latex 1 and being immobilized with the monoclonal antibody 2 having a different recognition site for the target substance from the antibody 1, and determining an amount of the substance based on the result of the agglutination reaction among the target substance, the latex1 and the latex2. Specifically, for example, the assay method for PSA used as the target substance is performed as follows. A specimen containing PSA and a reagent containing a monoclonal antibody to PSA immobilizing (carrying or sensitizing) latex having, for example, a mean particle size of 150 nm and a monoclonal antibody to PSA, which has a different recognition site from the above monoclonal antibody, immobilizing (sensitizing) a latex having, for example, a mean particle size of 280 nm are reacted; an extent of the thus generated agglutination is measured by photometry; and a concentration is determined from the previously prepared calibration curve of the standard substance. Wavelength for measurement of optical density is generally at 340-1000 nm, preferably at 500-900 nm. Measurement of the extent of agglutination is not limited to the photometry and can be selected from any known methods, such as the nephelometry and the counting immunoassay.

As described hereinabove, according to the immunoassay of the present invention, both target substances in the free form and the bound form can be assayed precisely in equimolar reaction. The equimolar reaction of the free form and the bound form in the present invention means the reaction binding the monoclonal antibody immobilized with latex to both forms in a ratio of approximately 1:1. Specifically, for example, the equimolar reaction in PSA can be defined as follows. The purified free form of PSA and the ACT-PSA bound form obtained from Stanford University are diluted stepwise and each solution is assayed. The theoretical values calculated by the designated value and the actual measured values are plotted on the X-axis and the Y-axis respectively, and a slope of the dilution straight line is obtained by the regression equation, and a ratio of both slopes (the slope of the free form PSA/the slope of the ACT-PSA bound form) is expressed as a deviation $\gamma$. When $\gamma$ ranges is $0.9 \leq \gamma < 1.1$, the reaction is regarded as the completely equimolar reaction. When $\gamma$ ranges is $0.8 \leq \gamma < 0.9$ and $1.1 \leq \gamma < 1.2$, the reaction is regarded as the nearly equimolar reaction (Symposium on 65th Meeting of the Japanese Urological Association).

The present invention will be further explained by using Examples, but the present invention is not limited by these Examples.

EXAMPLE

Example 1

Assay of Prostate-Specific Antigen (PSA) by Latex Immunonephelometry (1) Preparation of anti-human PSA antibody sensitized (immobilized) latex test solution With 0.5 ml of 50 mM borate buffer (pH 7.1) containing 0.3 mg of anti-human PSA mouse monoclonal antibody (clone No. PSA10) (Wako Pure Chemical Industries, Ltd.), 0.5 ml of 50 mM borate buffer (pH 7.1) suspended with polystyrene latex (mean particle size 0.22 μm or 0.28 μm, Sekisui Chemical Co. Ltd.) to adjust the concentration at 2% (W/V) was mixed, and the mixture was reacted at 25° C. for 2 hours. Thereafter, the latex isolated from the mixture by centrifugation was washed with 50 mM borate buffer (pH 7.1). The latex was suspended in 50 mM borate buffer (pH 7.3) containing 0.5% (W/V) of BSA to adjust the concentration of the latex at 1% (W/V), to obtain the anti-human PSA antibody sensitized latex test solution [1].

In the similar way hereinabove, 0.5 ml of 50 mM borate buffer (pH 7.1) containing 0.7 mg of anti-human PSA mouse monoclonal antibody (clone No. PSA14) (Wako Pure Chemical Industries, Ltd.) and 0.5 ml of 2% (W/V) polystyrene latex (mean particle size 0.12 μm or 0.15 μm, Sekisui Chemical Co. Ltd.) were mixed to prepare the anti-human PSA antibody sensitized latex test solution [2].

(2) Specimens

The standard sample of free form PSA and the standard sample of complex PSA (Stanford University) were diluted with 10 mM phosphate buffer (containing 0.85% NaCl, pH7.0) containing 1% BSA to prepare 25 ng/ml solution. The phosphate buffer is used as a blank reagent.

(3) Reagents

I. First Test solution

HEPES-NaOH buffer (pH 7.0) containing 0.1% BSA and 1% NaCl was prepared as the first test solution.

II. Second Test solution

Each of the anti-human PSA antibody sensitized latex test solutions [1] and [2] prepared in the above (1) was adjusted to 0.1% (W/V) of latex, and the both solutions were mixed in equal amount to prepare the second test solution.

(4) Assay method

Assay of PSA concentration was performed by using autoanalyzer (JOEL BM-8) under the following condition.
Specimen: 5 μl
First test solution: 90 μl
Second test solution: 30 μl
Assay method: 2 point end method (34-65)
Main wavelength: 571 nm (5) Results Optical densities (turbidities) obtained are shown in Table 1. The values in the table are indicated by 10,000-fold values of the obtained optical densities subtracted with the blank value. The deviation γ is a value dividing the slope of the free form PSA (measured value/theoretical value) by the slope of the complex PSA (measured value/theoretical value). When this value becomes the closer to 1.0, the more likely the equimolar binding of the antibody sensitized latex with the free form and the complex form occurs.

Comparative Example 1

Assay of PSA Using Latexes Having Equal Mean Particle Size

Latexes were prepared by the same method as in Example 1, and assay was performed by the same way as in Example 1, except that 0.5 ml of 50 mM borate buffer (pH 7.1) containing 0.6 mg each of two types of anti-human PSA mouse monoclonal antibody (clone Nos. PSA 10 and PSA 14) (Wako Pure Chemical Industries, Ltd.) and 0.5 ml of 50 mM borate buffer (pH 7.1) suspended with polystyrene latex (mean particle size 0.22 μm, Sekisui Chemical Co. Ltd.) to adjust the concentration at 2% (W/V) were mixed and reacted at 25° C. for 2 hours. The obtained results and deviation γ are shown in Table 1 together with the results of Example 1.

TABLE 1

|  | Example 1 | | | Comparative Example 1 |
|---|---|---|---|---|
| Particle size of antibody sensitized latex [1] | 0.28 μm | | 0.22 μm | 0.22 μm |
| Particle size of antibody sensitized latex [2] | 0.12 μm | 0.15 μm | 0.15 μm | 0.22 μm |
| Concentration of PSA (ng/ml) | | | | |
| Reagent blank Sensitivity (O.D. × 10,000) | −72 | −44 | −30 | −69 |
| Free PSA 25 ng/ml | 602 | 984 | 484 | 1,136 |
| Complex PSA 25 ng/ml | 629 | 898 | 426 | 825 |
| Deviation γ | 0.96 | 1.10 | 1.14 | 1.38 |

As obvious from Table 1, in the method combining with the latex having different mean particle size, the deviation shows approximately 1.0, indicating possible equimolar reaction with the free PSA and the complex PSA. Contrary to that, in the method combining with the latex having identical mean particle size, the deviation shows 1.38, indicating stronger reaction with the free PSA as compared with the complex PSA.

Example 2

(1) Standard Specimens

The standard sample of free form PSA and the standard sample of complex PSA (Stanford University) were diluted with 10 mM phosphate buffer (containing 0.85% NaCl, pH7.0) containing 1% BSA to prepare 0, 5, 10, 25 and 50 ng/ml solutions, respectively.

(2) Reagents

I. First Test Solution

The first test solution prepared in Example 1 was used.

II. Second Test Solution

In the antibody sensitized latexes prepared in Example 1, the antibody sensitized latex [1] was prepared using the latex having a mean particle size of 0.28 μm, and the antibody sensitized latex [2] was prepared using the latex having a mean particle size of 0.15 μm, and the solutions were mixed with the same way as in Example 1.

(3) Assay Method

Assay of PSA concentration was performed by using autoanalyzer (Toshiba Corp. TBA-120FR) under the following condition.

Specimen: 12 μl
First test solution: 120 μl
Second test solution: 40 μl
Assay method: 2 point end method (20-33)
Main wavelength: 572 nm (4) Results The optical densities (turbidities) obtained and the deviation r are shown in Table 2. The values in the table are indicated by 10,000-fold values of the measured optical densities subtracted with the blank value. The measured values in the table are values calculated by using the calibration curve prepared from the standard substance of free form PSA. A relationship between the measured optical densities of the free form PSA and the complex form PSA and each concentration (a graph) is shown in FIG. 1.

Comparative Example 2

Assay of PSA Using Latexes Having Equal Mean Particle Size

Assay was performed by the same way as in Example 2, except that two types of the antibody sensitized latex (mean particle size 0.22 μm) prepared in Comparative Example 1 were used. The obtained results and the deviation γ are shown in Table 2 together with the results of Example 2.

TABLE 2

|  | Example 2 | | Comparative Example 2 | |
|---|---|---|---|---|
| Particle size of antibody sensitized latex [1] | 0.28 μm | | 0.22 μm | |
| Particle size of antibody sensitized latex [2] | 0.15 μm | | 0.22 μm | |
| Concentration of PSA (ng/ml) | | | | |
| Reagent blank | 9 | | −23 | |
|  | Optical Density | Measured value(ng/ml) | Optical Density | Measured value(ng/ml) |
| Free PSA 5 | 298 | 5.0 | 300 | 5.0 |
| Complex PSA 5 | 291 | 4.9 | 239 | 4.0 |
| Free/Complex (%) |  | 102% |  | 125% |
| Free PSA 10 | 761 | 10.0 | 707 | 10.0 |
| Complex PSA 10 | 759 | 10.0 | 567 | 8.3 |
| Free/Complex (%) |  | 100% |  | 120% |
| Free PSA 25 | 2221 | 25.0 | 2293 | 25.0 |
| Complex PSA 25 | 2335 | 27.1 | 1751 | 19.9 |
| Free/Complex (%) |  | 92% |  | 126% |
| Free PSA 50 | 3580 | 50.0 | 4592 | 50.0 |
| Complex PSA 50 | 3755 | 53.2 | 4013 | 41.2 |
| Free/Complex (%) |  | 94% |  | 121% |
| Deviation γ |  | 0.93 |  | 1.22 |

In Table 2, in the method of combining use of the latexes having different mean particle sizes, since almost equimolar reaction is indicated in any concentration of PSA and the deviation 0.93 shows a value near to 1.0, it can be understood that the equimolar reaction system is substantially carried out. Further, in the case of using the latex having equal mean particle size, the reactivity of the free PSA is higher than the complex PSA in all concentrations, and the deviation exhibits 1.22, indicating no equimolar reaction.

This application is based on Japanese Patent Application serial No. JP2003-340028 filed in Japan Patent Office on Sep. 30, 2003, the contents of which are hereby incorporated by reference.

What is claimed is:

1. A reagent kit for an immunoassay of a target substance existing in a free form and a bound form in a specimen, comprising a reagent for the immunoassay comprising a first latex particle (1) which is immobilized with a first monoclonal antibody (1) for the target substance, and a second latex particle (2) which has a different mean particle size from the first latex particle (1) and is immobilized with a second monoclonal antibody (2) having a different recognition site for the target substance from the first monoclonal antibody (1), and a reagent for an agglutination accelerator, which accelerates an agglutination reaction between the first and second monoclonal antibodies and the target substance, comprising a copolymer obtained by polymerizing: a monomer represented by the following general formula: [2]:

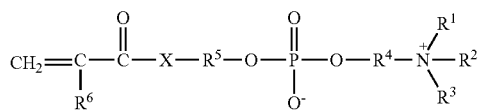

[2]

(wherein, R1-R3 are each independently a hydrogen atom or an alkyl group optionally having a hydroxyl group; R4 is an alkylene group; R5 is an alkylene group optionally having a substituent and optionally having an oxygen atom in the chain; R6 is a hydrogen atom or a methyl group; and X is an oxygen atom or a —NH- group), and benzyl methacrylate.

2. The kit according to claim 1, wherein the reagent for an agglutination accelerator farther comprises a nonspecific reaction suppressor.

3. The kit according to claim 2, wherein the target substance is prostate-specific antigen.

4. The kit according to claim 3, wherein the first latex particle (1) is one having the mean particle diameter of 0.05-0.18 μm and the second latex particle (2) is one having 0.18-0.5 μm.

5. The kit according to claim 1, wherein the first monoclonal antibody (1) has the acidic isoelectric point and the second monoclonal antibody (2) has the neutral isoelectric point, or the first monoclonal antibody (1) has the neutral isoelectric point and the second monoclonal antibody (2) has the acidic isoelectric point.

6. The kit according to claim 1, wherein the general formula is the following general formula: [5]:

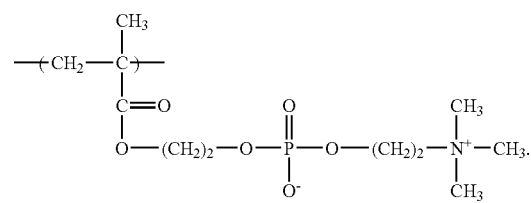

[5]

* * * * *